(12) United States Patent
Saroha et al.

(10) Patent No.: US 11,872,056 B2
(45) Date of Patent: Jan. 16, 2024

(54) ADVANCED CONTROL FEATURES FOR STEERING DEVICES FOR INTRAVASCULAR DEVICES AND ASSOCIATED SYSTEMS AND METHODS

(71) Applicant: KONINKLIJKE PHILIPS N.V., Eindhoven (NL)

(72) Inventors: Princeton Saroha, Ladera Ranch, CA (US); Jeremy Stigall, Carlsbad, CA (US); Maritess Minas, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 559 days.

(21) Appl. No.: 15/765,524

(22) PCT Filed: Oct. 7, 2016

(86) PCT No.: PCT/EP2016/074020
§ 371 (c)(1),
(2) Date: Apr. 3, 2018

(87) PCT Pub. No.: WO2017/060439
PCT Pub. Date: Apr. 13, 2017

(65) Prior Publication Data
US 2019/0076092 A1    Mar. 14, 2019

Related U.S. Application Data

(60) Provisional application No. 62/239,820, filed on Oct. 9, 2015.

(51) Int. Cl.
*A61B 5/00* (2006.01)
*A61B 8/08* (2006.01)
(Continued)

(52) U.S. Cl.
CPC .......... *A61B 5/6851* (2013.01); *A61B 5/0066* (2013.01); *A61B 5/027* (2013.01);
(Continued)

(58) Field of Classification Search
CPC ........ A61B 2034/301; A61M 25/0105; A61M 25/0136; A61M 2025/09116
See application file for complete search history.

(56) References Cited

U.S. PATENT DOCUMENTS 6,402,726 B1 *  6/2002  Genese .............. A61M 25/0113
251/4
2003/0045778 A1  3/2003  Ohline et al.
(Continued)

FOREIGN PATENT DOCUMENTS

JP           5023296 A     2/1993
WO      2015041877 A1     3/2015

*Primary Examiner* — Puya Agahi

(57) ABSTRACT

Handheld steering devices for use with intravascular devices and associated systems and methods are disclosed. In some instances, the handheld steering device includes a housing sized and shaped for grasping by a hand of a user; a steering controller coupled to the housing; a processor in communication with the steering controller, the processor configured to translate inputs from the steering controller into actuation signals based on a code architecture that includes a script for at least one of a return home function, a return to stored position function, a store current position function, or an automated mapping function; and an actuator positioned within the housing and configured to interface with the intravascular device based on the actuation signals to steer the intravascular device. Associated systems and methods are also disclosed.

15 Claims, 10 Drawing Sheets

(51) Int. Cl.

| | | |
|---|---|---|
| *A61B 8/12* | (2006.01) | |
| *A61B 5/027* | (2006.01) | |
| *A61B 34/00* | (2016.01) | |
| *A61B 8/00* | (2006.01) | |
| *A61M 25/01* | (2006.01) | |
| *A61B 90/00* | (2016.01) | |
| *A61B 34/30* | (2016.01) | |
| *A61B 5/0215* | (2006.01) | |

(52) U.S. Cl.
CPC .......... *A61B 5/6852* (2013.01); *A61B 8/0891* (2013.01); *A61B 8/12* (2013.01); *A61B 34/70* (2016.02); *A61B 5/0215* (2013.01); *A61B 8/445* (2013.01); *A61B 34/76* (2016.02); *A61B 2034/301* (2016.02); *A61B 2034/742* (2016.02); *A61B 2090/064* (2016.02); *A61M 25/0136* (2013.01)

(56) References Cited

U.S. PATENT DOCUMENTS

| | | | |
|---|---|---|---|
| 2007/0225641 A1* | 9/2007 | Schneider | A61M 25/0136 604/93.01 |
| 2009/0287203 A1* | 11/2009 | Mazzone | A61M 25/1038 606/21 |
| 2010/0074403 A1 | 3/2010 | Inglese | |
| 2010/0204613 A1 | 8/2010 | Rollins et al. | |
| 2013/0261540 A1 | 10/2013 | Crank | |
| 2014/0180124 A1 | 6/2014 | Whiseant et al. | |
| 2015/0073340 A1 | 3/2015 | Pacheco et al. | |
| 2015/0094654 A1* | 4/2015 | Bansal | A61M 25/0147 604/95.04 |

\* cited by examiner

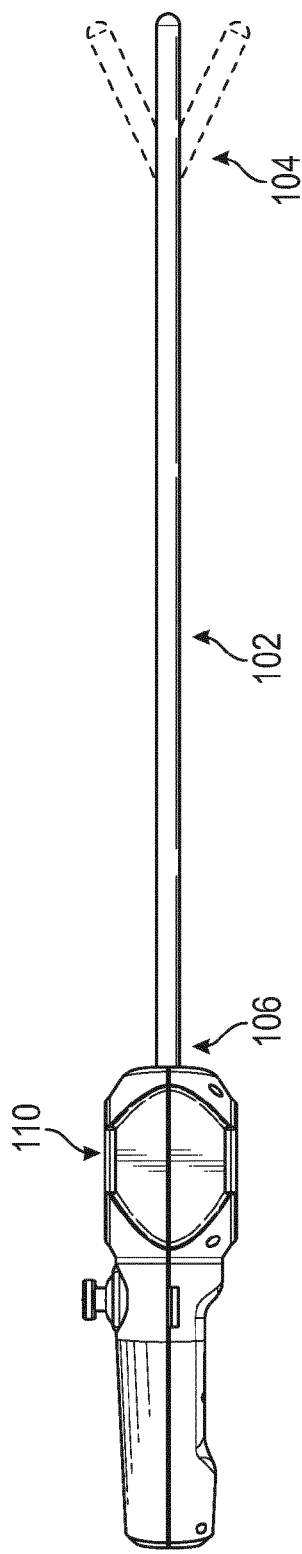
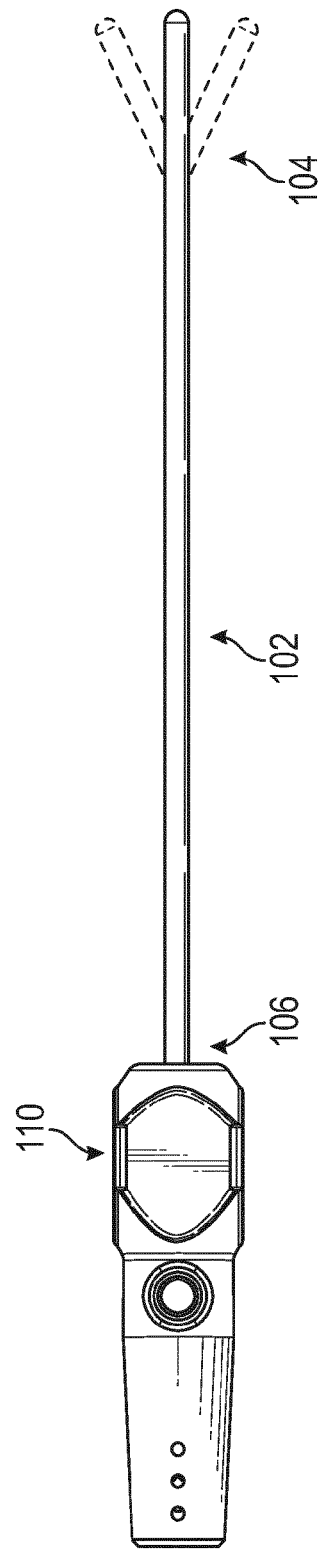
FIG. 2
FIG. 3

ADVANCED CONTROL FEATURES FOR STEERING DEVICES FOR INTRAVASCULAR DEVICES AND ASSOCIATED SYSTEMS AND METHODS

This application is the U.S. National Phase application under 35 U.S.C. § 371 of International Application No. PCT/EP2016/074020, filed on Oct. 7, 2016, which claims the benefit of Provisional Application Ser. No. 62/239,820, filed Oct. 9, 2015. These applications are hereby incorporated by reference herein.

TECHNICAL FIELD

The present disclosure relates to steering devices for use with intravascular devices used in the diagnosis and treatment of various maladies. In particular, some embodiments disclosed herein are particularly suited for use in intravascular and intracardiac diagnostic procedures and/or treatments.

BACKGROUND

Innovations in diagnosing and verifying the level of success of treatment of disease have migrated from external imaging processes to internal diagnostic processes. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intracardiac echocardiography (ICE), intravascular ultrasound (IVUS), forward looking IVUS (FL-IVUS), pressure sensing (including associated fractional flow reserve (FFR) and instant wave-free ration (iFR) calculations), flow sensing (velocity and/or volumetric measurements, including associated coronary flow reserve (CFR) calculations), optical coherence tomography (OCT), trans-esophageal echocardiography, and various image-guided therapies. Each of these techniques may be better suited for different diagnostic and/or therapeutic situations. To increase the chance of successful treatment, health care facilities may have a multitude of imaging, treatment, diagnostic, and/or sensing modalities on hand in a catheter lab during a procedure. In order to properly use any of the imaging, treatment, diagnostic, and/or sensing modalities, the associated device must be accurately guided to the region of interest within the patient in a controlled manner without causing damage to the anatomy of the patient.

Accordingly, there remains a need for improved intravascular devices, systems, and methods to facilitate the guidance of one or more imaging, treatment, diagnostic, and/or sensing components to a region of interest within a patient.

SUMMARY

Embodiments of the present disclosure are directed to steering devices for use with intravascular devices, including associated systems and methods.

An intravascular steering device is provided that includes a housing sized and shaped for grasping by a hand of a user, the housing including a proximal portion and a distal portion, wherein the distal portion includes an opening sized and shaped to receive an intravascular device; a steering controller coupled to the housing; a processor in communication with the steering controller, the processor configured to translate inputs from the steering controller into actuation signals based on a code architecture, wherein the code architecture includes a script for at least one of a return home function, a return to stored position function, a store current position function, or an automated mapping function; and an actuator positioned within the housing and in communication with the processor such that the actuator receives the actuation signals from the processor, the actuator configured to interface with the intravascular device based on the actuation signals to the steer the intravascular device.

The steering controller can include a joystick. The actuator can include a first mechanism for controlling movement in a first dimension; and a second mechanism for controlling movement in a second dimension perpendicular to the first dimension. The actuator can further include a third mechanism for controlling movement in a third dimension, the third dimension being perpendicular to the first and second dimensions. The actuator can further include a mechanism for controlling rotation of the intravascular device about a longitudinal axis of the intravascular device. The processor can be positioned within the housing or remote from the housing. The intravascular steering device can further include a haptic feedback device positioned within the housing and configured to provide an alert to a user when a force on the intravascular device exceeds a threshold. The force on the intravascular device can be measured by at least one of a sensor within the housing or a sensor within the intravascular device. The intravascular steering device can further include a rechargeable power supply positioned within the housing; and a wireless transceiver positioned within the housing.

An intravascular steering system is also provided that includes an intravascular device having a proximal section and a distal section, wherein at least one sensing component is coupled to the distal section; and an intravascular steering device having: a housing sized and shaped for grasping by a hand of a user, the housing including a proximal portion and a distal portion, wherein the distal portion includes an opening sized and shaped to receive the proximal section of the intravascular device; a steering controller coupled to the housing; a processor in communication with the steering controller, the processor configured to translate inputs from the steering controller into actuation signals based on a code architecture, wherein the code architecture includes a script for at least one of a return home function, a return to stored position function, a store current position function, or an automated mapping function; and an actuator positioned within the housing and in communication with the processor such that the actuator receives the actuation signals from the processor, the actuator configured to interface with the intravascular device based on the actuation signals to the steer the intravascular device.

A method of steering an intravascular device is also provided that includes providing an intravascular steering device having: a housing sized and shaped for grasping by a hand of a user, the housing including a proximal portion and a distal portion, wherein the distal portion includes an opening sized and shaped to receive the proximal section of the intravascular device; a steering controller coupled to the housing; a processor in communication with the steering controller, the processor configured to translate inputs from the steering controller into actuation signals based on a code architecture, wherein the code architecture includes a script for at least one of a return home function, a return to stored position function, a store current position function, or an automated mapping function; and an actuator positioned within the housing and in communication with the processor such that the actuator receives the actuation signals from the processor, the actuator configured to interface with the intravascular device based on the actuation signals to the steer the intravascular device; coupling an intravascular device to the intravascular steering device by introducing a proximal section of the intravascular device into the opening in the housing; and utilizing the intravascular steering device to guide the intravascular device to a target location within a patient.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 2 is a side view of the intravascular system of FIG. 1 showing steering of the intravascular device by the handheld steering device in a first dimension (e.g., up and down).

FIG. 3 is a top view of the intravascular system of FIGS. 1 and 2 showing steering of the intravascular device by the handheld steering device in a second dimension (e.g., left and right), the second dimension being perpendicular to the first dimension shown in FIG. 2.

Figure 1:
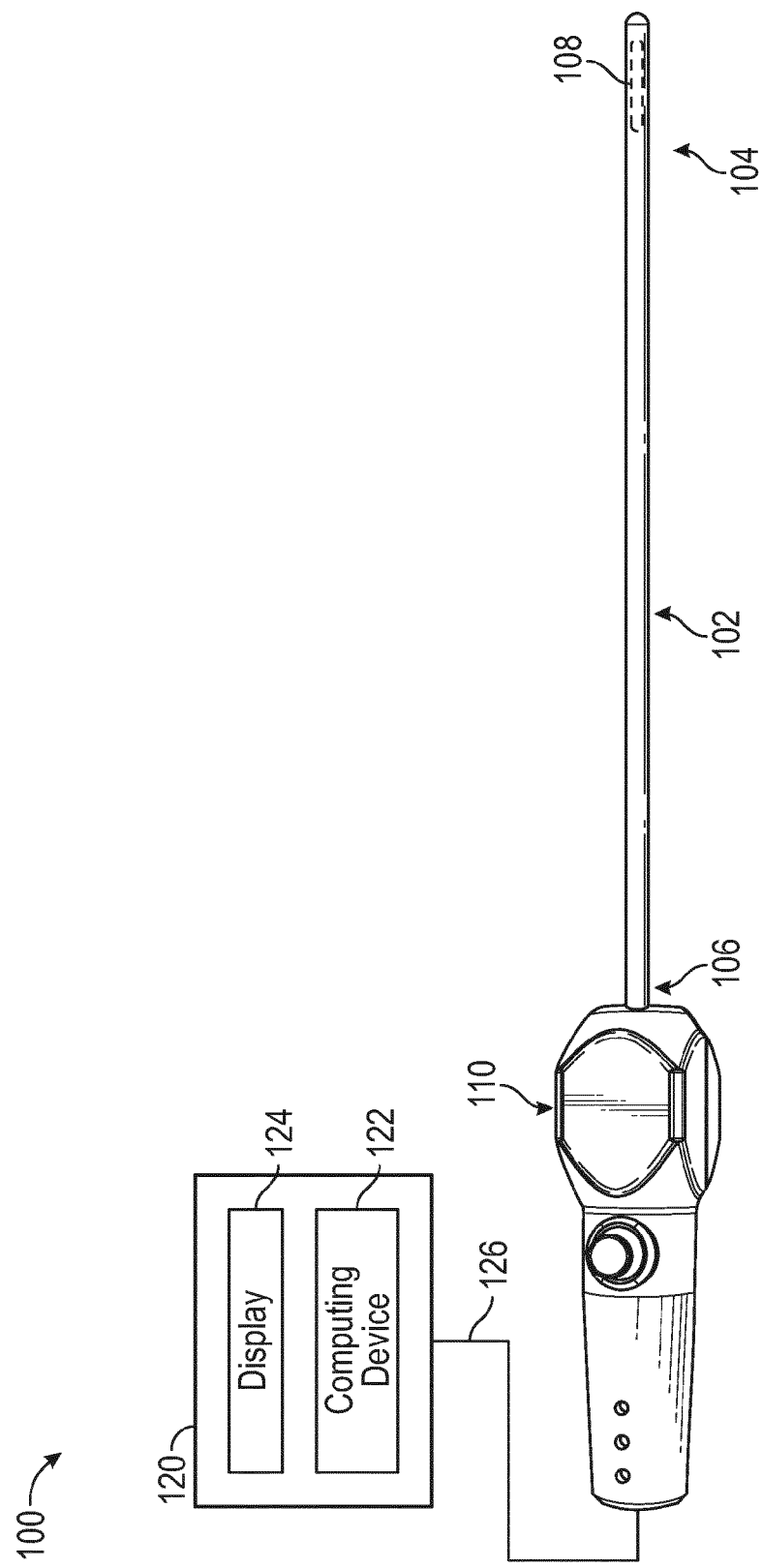
FIG. 1 is a perspective view of an intravascular system including a handheld steering device, an intravascular device, and a processing system according to the present disclosure.

For clarity of discussion, elements having the same designation in the drawings may have the same or similar functions. The drawings may be better understood by referring to the following Detailed Description.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "flexible elongate member" or "elongate flexible member" includes at least any thin, long, flexible structure that can be inserted into the vasculature of a patient. While the illustrated embodiments of the "flexible elongate members" of the present disclosure have a cylindrical profile with a circular cross-sectional profile that defines an outer diameter of the flexible elongate member, in other instances all or a portion of the flexible elongate members may have other geometric cross-sectional profiles (e.g., oval, rectangular, square, elliptical, etc.) or non-geometric cross-sectional profiles. Flexible elongate members include, for example, guide wires and catheters. In that regard, catheters may or may not include a lumen extending along its length for receiving and/or guiding other instruments. If the catheter includes a lumen, the lumen may be centered or offset with respect to the cross-sectional profile of the device.

In most embodiments, the flexible elongate members of the present disclosure include one or more electronic, optical, or electro-optical components. For example, without limitation, a flexible elongate member may include one or more of the following types of components: a pressure sensor, a flow sensor, a temperature sensor, an imaging element, an optical fiber, an ultrasound transducer, a reflector, a mirror, a prism, an ablation element, an RF electrode, a conductor, and/or combinations thereof. Generally, these components are configured to obtain data related to a vessel or other portion of the anatomy in which the flexible elongate member is disposed. Often the components are also configured to communicate the data to an external device for processing and/or display. In some aspects, embodiments of the present disclosure include imaging devices for imaging within the lumen of a vessel, including both medical and non-medical applications. However, some embodiments of the present disclosure are particularly suited for use in the context of human vasculature. Imaging of the intravascular space, particularly the interior walls of human vasculature can be accomplished by a number of different techniques, including ultrasound (often referred to as intravascular ultrasound ("IVUS") and intracardiac echocardiography ("ICE")) and optical coherence tomography ("OCT"). In other instances, infrared, thermal, or other imaging modalities are utilized.

The electronic, optical, and/or electro-optical components of the present disclosure are often disposed within a distal portion of the flexible elongate member. As used herein, "distal portion" of the flexible elongate member includes any portion of the flexible elongate member from the mid-point to the distal tip. As flexible elongate members can be solid, some embodiments of the present disclosure will include a housing portion at the distal portion for receiving the electronic components. Such housing portions can be tubular structures attached to the distal portion of the elongate member. Some flexible elongate members are tubular and have one or more lumens in which the electronic components can be positioned within the distal portion.

The electronic, optical, and/or electro-optical components and the associated communication lines are sized and shaped to allow for the diameter of the flexible elongate member to be very small. For example, the outside diameter of the elongate member, such as a guide wire or catheter, containing one or more electronic, optical, and/or electro-optical components as described herein are between about 0.0007" (0.0178 mm) and about 0.118" (3.0 mm), with some particular embodiments having outer diameters of approximately 0.014" (0.3556 mm), approximately 0.018" (0.4572 mm), and approximately 0.035" (0.889 mm). As such, the flexible elongate members incorporating the electronic, optical, and/or electro-optical component(s) of the present application are suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which an element is directly secured to another element, such as being glued or otherwise fastened directly to, on, within, etc. another element, as well as indirect techniques of securing two elements together where one or more elements are disposed between the secured elements.

Referring now to FIG. 1, shown therein is a system 100 that includes an intravascular device 102, a steering device 110, and a processing system 120. As discussed in greater detail below, a proximal portion of the intravascular device 102 is engaged with the steering device 110 such that the steering device 110 can be utilized to steer a distal portion of the intravascular device 102. In this regard, the steering device 110 provides a user with an ergonomic and intuitive controller for accurately and precisely controlling the movement of a disposable intravascular device (e.g., multi-planar steering, withdrawal, advancement, rotational, and/or combinations thereof) within a patient. As a result, the system 100 and steering device 110 provide many advantages and improvements over existing approaches, including without limitation: single hand operation/control in all actuation directions, simple and intuitive functional interface, improved actuation precision including speed and angle differentiation, fast yet controlled actuation response, minimum user force input required for actuation (actuation strength limited by motor specifications instead of user comfort), ability to use with many different types of intravascular devices with varying profiles/characteristics, safety lock and return to neutral position functionalities, minimum bend radius, reduced body sway when actuating the distal tip, better torque response, disposable, lower cost, easier manufacturability and assembly, modular componentry to facilitate simple manufacture and/or assembly of numerous specialized devices.

The system 100 and steering device 110 can also be implemented with various advanced control features to further improve the functionality of the device and associated user experience. For example, the system 100 can utilize processor-implemented control functionalities to further enhance the capabilities of the steering device 110, including features such as a return home function, a return to stored position function, a store current position function, an automated mapping function, an auto lock function, a variable speed function, a multi-level actuation function, a hysteresis compensation function, a calibration function, a remote control function, and/or combinations thereof. Further, the system 100 and steering device 110 may include one or more of the following features: memory for storing and recalling position(s) and/or actuation angle(s) in a controlled manner, including allowing the setting of different positions as the neutral intravascular device position, providing the user accurate feedback on the intravascular device's position/actuation angle relative to home (neutral) position, allowing control of the steering device by a remote user (e.g., at the system console, in a separate room, and/or across the world), multi-level actuation controls (e.g., coarse, fine, etc.), logging actuation usage for complaint handling and/or case documentation, providing automated 3D anatomical mapping of the vessels, heart, or other structures when used in conjunction with intravascular devices having imaging elements, and producing more consistent device control through in line calibrations for both first time device use and repeated uses after reprocessing, which can reduce unit to unit variation and compensate for the effects of wear and tear on the steering device and/or intravascular device.

The intravascular device 102 includes a flexible elongate member having a distal portion 104 adjacent a distal end and a proximal portion 106 adjacent a proximal end. A component 108 is positioned within the distal portion 104 of the flexible elongate member proximal of the distal end. Generally, the component 108 is representative of one or more electronic, optical, or electro-optical components. In that regard, the component 108 can include an imaging element, an optical fiber, an ultrasound transducer, a reflector, a mirror, a prism, an ablation element, an RF electrode, a pressure sensor, a flow sensor, a temperature sensor, a conductor, and/or combinations thereof. The specific type of component or combination of components can be selected based on an intended use of the intravascular device. In some instances, the component 108 is positioned less than 10 cm, less than 5, or less than 3 cm from the distal tip 105. In some instances, the component 108 is positioned within a housing of the intravascular device 102. In that regard, the housing is a separate component secured to the flexible elongate member in some instances. In other instances, the housing is integrally formed as a part of the flexible elongate member.

In some instances, the intravascular device 102 also includes a connector adjacent the proximal portion 106 of the device. In that regard, the connector can be at the proximal end of the flexible elongate member or spaced from the proximal end of the flexible elongate member. Generally, the spacing from the proximal end can be between 0% and 50% of the total length of the flexible elongate member. While the total length of the flexible elongate member can be any length, in some embodiments the total length is between about 1300 mm and about 4000 mm, with some specific embodiments having a length of 1400 mm, 1900 mm, and 3000 mm. Accordingly, in some instances the connector is positioned at the proximal end. In other instances, the connector is spaced from the proximal end. For example, in some instances the connector is spaced from the proximal end between about 0 mm and about 1400 mm. In some specific embodiments, the connector is spaced from the proximal end by a distance of 0 mm, 300 mm, and 1400 mm. In some implementations, the connector is positioned at or adjacent to the proximal end of the intravascular device 102 such that the connector engages a mating connector within the steering device 110 when the intravascular device 102 is coupled with the steering device 110. In other implementations, the connector is spaced from the proximal end of the intravascular device 102 such that the connector is positioned outside of the steering device 110 when the intravascular device 102 is coupled with the steering device 110, which can allow selective coupling of the connector to a mating connector separate from the steering device 110.

The connector is configured to facilitate communication between the intravascular device 102 and another device. More specifically, in some embodiments the connector is configured to facilitate communication of data obtained by the component 108 to another device, such as a computing device or processor. Accordingly, in some embodiments the connector is an electrical connector. In such instances, the connector provides an electrical connection to one or more electrical conductors that extend along the length of the intravascular device 102 and are electrically coupled to the component 108. In some embodiments the electrical conductors are embedded within a core of the flexible elongate member. In other embodiments, the connector is an optical connector. In such instances, the connector provides an optical connection to one or more optical communication pathways (e.g., fiber optic cable) that extend along the length of the intravascular device 102 and are optically coupled to the component 108. Similarly, in some embodiments the optical fibers are embedded within a core of the flexible elongate member. Further, in some embodiments the connector provides both electrical and optical connections to both electrical conductor(s) and optical communication pathway(s) coupled to the component 108. In that regard, it should be noted that component 108 can be comprised of a plurality of elements. The connector can be configured to provide a physical connection to another device, either directly or indirectly. The connector can also be configured to facilitate wireless communication between the intravascular device 102 and another device. Generally, any current or future developed wireless protocol(s) may be utilized. In yet other instances, the connector facilitates both physical and wireless connection to another device.

As noted above, in some instances the connector provides a connection between the component 108 of the intravascular device 102 and an external device. Accordingly, in some embodiments one or more electrical conductors, one or more optical pathways, and/or combinations thereof extend along the length of the intravascular device 102 between the connector and the component 108 to facilitate communication between the connector and the component 108. Generally, any number of electrical conductors, optical pathways, and/or combinations thereof can extend along the length of the intravascular device 102 between the connector and the component 108, embedded in the core or not. In some instances, between one and ten electrical conductors and/or optical pathways extend along the length of the intravascular device 102 between the connector at the proximal portion 106 and the component 108 at the distal portion 104. The number of communication pathways and the number of electrical conductors and optical pathways extending along the length of the intravascular device 102 is determined by the desired functionality of the component 108 and the corresponding elements that define component 108 to provide such functionality.

As noted above, the steering device 110 is configured to control movement of the distal portion 104 of the intravascular device 102 by interfacing with the proximal portion 106 of the intravascular device 102. In this regard, the steering device 110 can be configured to control movement of the distal portion 104 of the intravascular device 102 in one or more dimensions. For example, FIGS. 2-5 show various types of movements that can be controlled by the steering device 110. Referring to FIG. 2, the steering device 110 is shown controlling movement of the distal portion 104 of the intravascular device 102 in a first dimension (e.g., up and down relative to the steering device 110). Referring to FIG. 3, the steering device 110 is shown controlling movement of the distal portion 104 of the intravascular device 102 in a second dimension (e.g., left and right relative to the steering device 110) that is perpendicular to the dimension shown in FIG. 2. While FIGS. 2 and 3 show particular, exemplary deviations of the distal portion 104 of the intravascular device 102 in the noted dimensions, it is understood that actuation of the steering device 110 in a particular direction can cause the distal tip of the intravascular device 102 to move between 0 degrees and 180 degrees (or more) in that direction depending on the amount of actuation imparted by the user. Accordingly, in some implementations continued actuation of the steering device 110 in a particular direction can cause the distal portion 104 of the intravascular device 102 to contact and/or loop next to a more proximal portion of the intravascular device 102.

Figure 4:
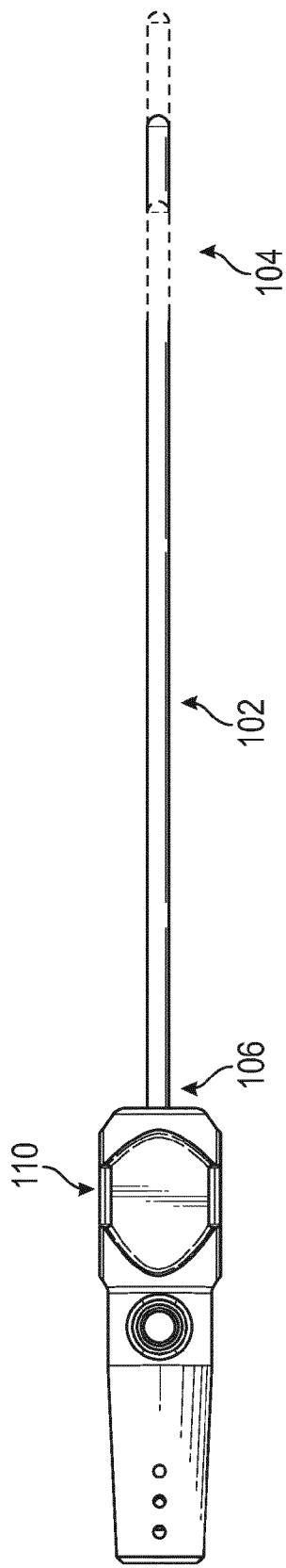
FIG. 4 is a top view of the intravascular system of FIGS. 1-3 showing translation of the intravascular device by the handheld steering device in a third dimension (e.g., forward and backward), the third dimension being perpendicular to the first and second dimensions shown in FIGS. 2 and 3.

Referring to FIG. 4, the steering device 110 is shown controlling movement of the distal portion 104 of the intravascular device 102 in a third dimension (e.g., forward and backward relative to the steering device 110) that is perpendicular to the dimensions shown in FIGS. 2 and 3. In particular, FIG. 4 shows the steering device 110 controlling translation of the intravascular device 102 along a longitudinal axis of the intravascular device. In some implementations, the steering device 110 can be utilized to precisely control the advancement or retraction of the intravascular device 102 through a patient, including the distance, speed, and/or combination thereof. In this regard, the steering device 110 can be utilized to perform pullback procedures to obtain data over a length of a region of interest within the patient.

Figure 5:
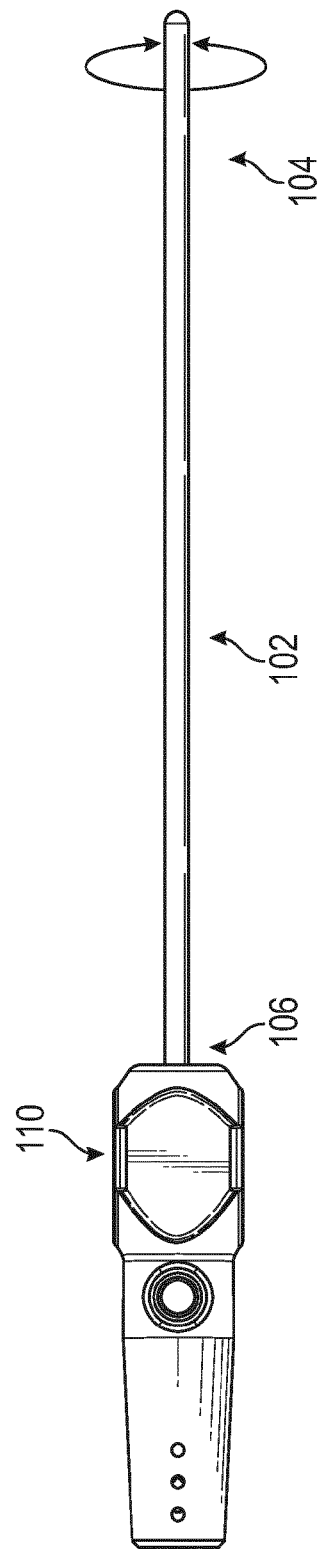
FIG. 5 is a top view of the intravascular system of FIGS. 1-4 showing rotation (e.g., clockwise and/or counter-clockwise) of the intravascular device by the handheld steering device.

Referring to FIG. 5, the steering device 110 is shown controlling rotation of the distal portion 104 of the intravascular device 102 about a longitudinal axis of the intravascular device. In some implementations, the steering device 110 can be utilized to precisely control the rotational position of the distal portion 104 of the intravascular device 102 to facilitate aiming or positioning of the distal portion 104 of the intravascular device in a desired manner. For example, this can be useful for ablation procedures, repositioning a sensing element (e.g., when an ambient opening for a pressure sensor is positioned against a vessel wall, rotation of the distal portion of the intravascular device can move the opening towards the center of the vessel to improve the accuracy of pressure measurements), and/or other instances where a rotational orientation of the intravascular device 102 can affect the diagnosis and/or treatment.

The steering device 110 can be configured to control movement of the distal portion 104 of the intravascular device 102 in one or more of the manners shown in FIGS. 2-5, including all of them in some implementations. The particular movement(s) that the steering device 110 is configured to control may be selected based on the type(s) of intravascular devices the steering device is to be used with, user preference, and/or other factors.

Many of the advanced control features of the present application can be applied to a wide range of intravascular steering devices, including handheld devices, surgical robots, and/or combinations thereof to further improve the functionality of the steering device(s). Accordingly, while the features may be described below in the context of handheld steering device 110, it is understood that the features may also be utilized with numerous other types of intravascular steering devices without departing from the scope of the present disclosure.

Figure 6A:
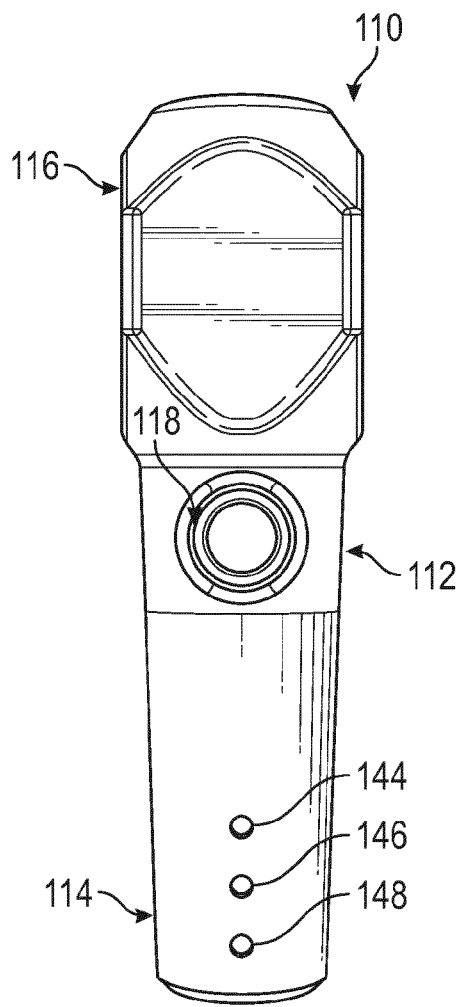
FIG. 6A is a top view of the handheld steering device of FIGS. 1-5.
Figure 6B:
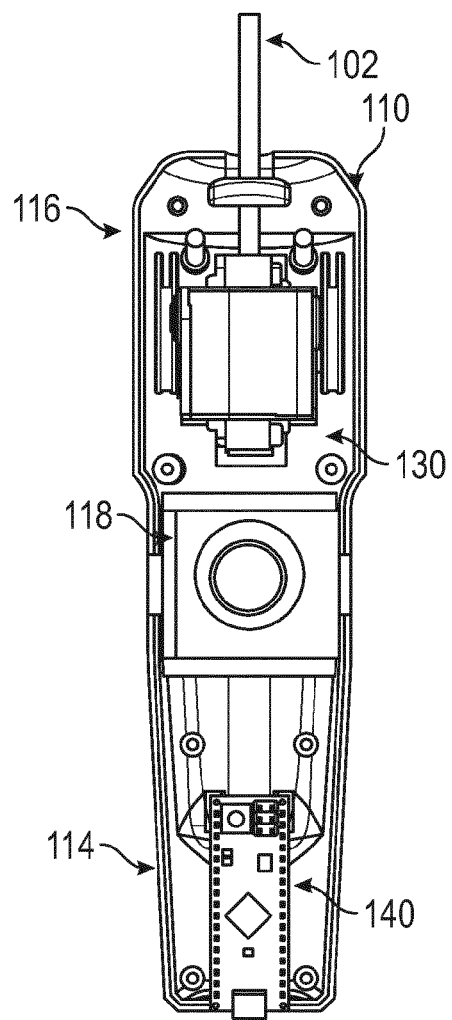
FIG. 6B is a top view of the handheld steering device similar to that of FIG. 6A, but with a top portion of a housing of the handheld steering device removed to reveal inner components of the handheld steering device and showing an intravascular device engaged with the handheld steering device.

Referring now to FIGS. 6A and 6B, additional details of the steering device 110 will be described. Referring initially to FIG. 6A, the steering device 110 includes a housing 112 having a proximal portion 114 and a distal portion 116. The housing 112 is sized and shaped for grasping by a single hand of a user. It is understood that the housing 112 may have many different geometries suitable for handheld use other than those shown in the present disclosure. The steering device 110 also includes a steering controller 118 coupled to the housing 112. The steering controller 118 can be any suitable type of controller including without limitation a joystick (as shown), dial, track pad, scroll wheel, touchscreen, and/or combinations thereof. In short, the steering controller 118 should be able to receive user inputs indicative of a desired movement of the distal portion 104 of the intravascular device 102. The steering controller 118 may include multiple controls in some instances. For example, the steering controller 118 may include separate control for each dimension or a separate control for a combination of dimensions (e.g., a control for x-y movements).

A single thumb joystick can be particular suitable for controlling steering of the distal portion of the intravascular device 102 in all directions. In this regard, the joystick circuit can include a biaxial potentiometer design with a digital button pin press function. The joystick circuit can be connected to a microcontroller. Through software and/or firmware coding, a variety of functions can be controlled through a single joystick. For example, the use of a single click, double clicks, press for duration, etc. can be utilized to toggle the joystick between different functions/controls. However, additional buttons controlling specific handle functionalities (e.g. on/off switch, lock button, etc.) can be included in addition to the joystick for user convenience and ease of use.

The steering device 110 includes an actuator 130 to impart the desired forces on the intravascular device 102 for steering. It is understood that the actuator 130 can include various types of electro-mechanical, mechanical, pneumatic, optical-mechanical components, and/or combinations thereof to impart forces on the proximal portion 106 of the intravascular device 102 to control the movement of the distal portion 104 of the intravascular device 102 in the desired direction(s). In some implementations, the actuator 130 includes one or more motors that impart movement and/or forces onto other components. In some instances, it is desirable to have motors that can be precisely controlled in terms of rotor position, force, response time, etc. Accordingly, the motor(s) can include stepper motors, servo motors, and/or other suitable motors in some implementations. Some exemplary steering device arrangements are described in U.S. patent application Ser. No. 14/135,310, filed Dec. 19, 2013, each of which is hereby incorporated by reference in its entirety.

As shown in FIG. 6B, the steering device 110 can also include a microcontroller 140. The microcontroller 140 can be utilized to control the logic and store the data and/or program code necessary for actuation and/or advanced features of the steering device 110. In this regard, it is understood that the microcontroller 140 can include a processor, which may be implemented using a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The processor may also be implemented as a combination of computing devices, e.g., a combination of a DSP and a microprocessor, a plurality of microprocessors, one or more microprocessors in conjunction with a DSP core, or any other such configuration.

It is also understood that the microcontroller 140 can include memory, which may include random access memory (RAM), read-only memory (ROM), flash memory devices in RAM, optical storage media, erasable programmable read-only memory (EPROM), registers, or combinations thereof, including a non-transitory computer-readable medium. Instructions or code may be stored in the memory of the microcontroller 140 that are executable by a processor of the microcontroller. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The microcontroller 140 can power the motors and/or other components of the actuator 130 needed for the full range of steering actuations provided by the steering device 110. The microcontroller 140 can be powered through a wired interface with an external device (e.g., processing system 120, a console, etc.) or via a rechargeable power supply (e.g., one or more batteries, capacitors, etc.) within the housing 112. To this end, the power supply can be mounted within and/or removably coupled to the housing 112.

As shown in FIG. 6A, the steering device 110 can include indicator lights 144, 146, and 148. The indicator lights 144, 146, and 148 can provide various indications to the user as to the state of the steering device 110 and/or the intravascular device 102. The indicator lights 144, 146, and 148 may be provided in addition to other notifications to the user, for example via a graphical user interface on the display 124 of the processing system 120. As discussed below, the indicator lights can provide a wide variety of notifications to the user, include without limitation: on/off, device at HOME position, device at STORED position, device moving to HOME, device moving to STORED position, device position locked, motor(s) at maxed position in a particular direction, etc. In this regard, the indicator lights 144, 146, and 148 can be part of or in communication with the microcontroller 140 such that the microcontroller 140 controls the activation/status of the indicator lights 144, 146, and 148.

In addition to and/or in lieu of the indicator lights 144, 146, and 148, the steering device 110 can include other indicators, including audible and tactile notifications. For example, in some implementations the steering device 110 is configured to provide force feedback to the user based on force sensors at the distal portion of the intravascular device (monitoring the amount of force/compression on the distal portion of the intravascular device) and/or force sensors monitoring the amount of tension of the pull-wires and/or the pull-wire wheel anchors. The force measurement(s) can then be conveyed to the user via one or more vibration motors to create haptic feedback (vibration location and magnitude can vary depending on the sensor(s) detecting a force exceeding predefined thresholds and/or the magnitude of the force measurement). The force measurements can also be conveyed to the user via a graphical user interface on the display 124 of the processing system 120, via illumination of one or more of the indicator lights 144, 146, and 148, and/or an audible warning/alarm. Actuator force measurements (e.g., tension, pressure, etc.) can also be used to identify if a particular steering device 110 needs to be calibrated/refurbished by identifying significant drop offs in the maximum actuation forces at the maximum motor ranges when compared to the values from original calibration/use.

The steering device 110 can be configured to communicate with one or more external devices and/or processing systems, such as processing system 120. In this regard, the communications with the external devices and/or processing systems can be utilized to control operation of the steering device 110, provide feedback on the steering/actuations imparted by the steering device, and/or receive data from sensing elements associated with the intravascular device 102 and/or steering device 110. It is understood that any communication pathway 126 between the steering device 110 and the external devices and/or processing systems may be utilized, including physical connections (including electrical, optical, and/or fluid connections), wireless connections, and/or combinations thereof. In that regard, it is understood that the communication pathway 126 is wireless in some instances. As such, the microcontroller 140 can include or be in communication with a wireless transceiver positioned within the housing 112 to facilitate such wireless communications. In some instances, the communication pathway 126 includes a communication link over a network (e.g., intranet, internet, telecommunications network, and/or other network). In that regard, it is understood that the external devices and/or processing systems, such as processing system 120, can be positioned remote from a procedure room where the steering device 110 is being used. Having the communication pathway 126 include a connection over a network can facilitate communication between the steering device 110 and the external devices and/or processing systems regardless of whether the external devices and/or processing systems are in an adjacent room, an adjacent building, or in a different state/country. Further, it is understood that the communication pathway 126 between the steering device 110 and the external devices and/or processing systems can a secure connection. Further still, it is understood that the data communicated over one or more portions of the communication pathway 126 between the steering device 110 and the external devices and/or processing systems can be encrypted.

Referring now to FIGS. 7-13, various aspects of controlling a steering device according to the present disclosure will be discussed. In particular, FIGS. 7-13 provide flow charts illustrating various advanced control features for steering devices in accordance with the present disclosure. The flow charts are provided as an exemplary implementation of these control features and in no way limit the manner in which the features may be implemented. For example, it is understood the blocks/steps may be performed in different orders and that additional blocks/steps may be inserted before, after, and/or between the blocks/steps of each flow chart. Further, it is understood that the various control features may be used individually and/or in combination with one another.

Further still, it is understood that the control features described with respect to FIGS. 7-13 may be implemented using a processor and/or memory, which may be part of the steering device 110, the processing system 120, and/or another device in communication with the steering device 110 and/or the processing system 120. Instructions or code may be stored in the memory that are executable by the processor for carrying out the control feature(s). The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements. Further, processor can include a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. The processor may also be implemented as a combination of computing devices, e.g., a combination of a DSP and a microprocessor, a plurality of microprocessors, one or more microprocessors in conjunction with a DSP core, or any other such configuration. Similarly, the memory can include random access memory (RAM), read-only memory (ROM), flash memory devices in RAM, optical storage media, erasable programmable read-only memory (EPROM), registers, or combinations thereof, including a non-transitory computer-readable medium.

Figure 7:
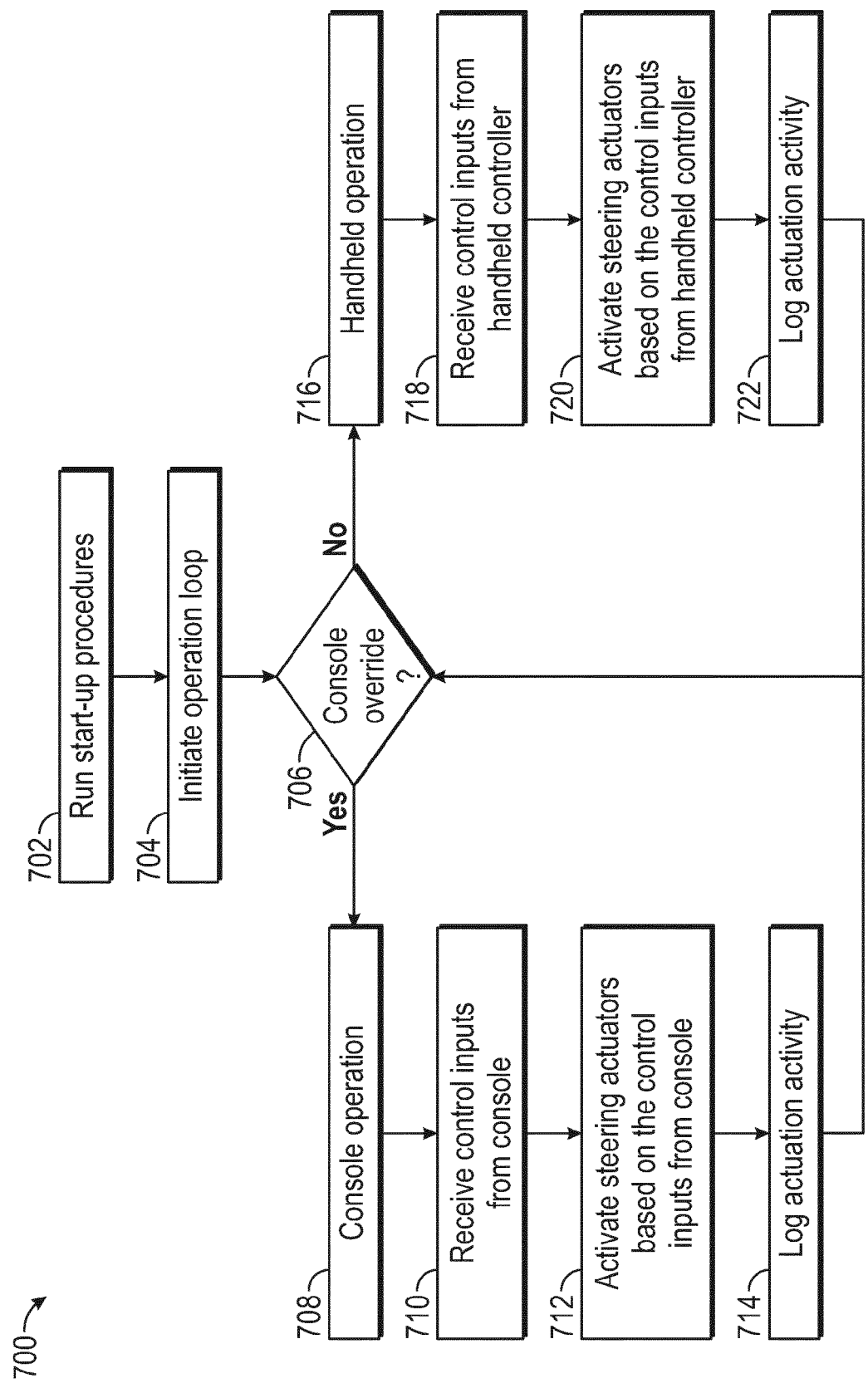
FIG. 7 is a flow chart illustrating aspects of controlling a steering device according to the present disclosure.

Referring now to FIG. 7, shown therein is a flow chart illustrating aspects of a method 700 of controlling a steering device according to the present disclosure. At block 702, the method 700 includes running a start-up procedure. The start-up procedure can include: providing power to the steering device 110, including activating the steering controller 118, actuator 130, microcontroller 140, and/or indicator lights 144, 146, and 148, establishing communication and/or verifying communication between the components of the steering device 110 (e.g., between the steering controller 118 and microcontroller 140, between the microcontroller 140 and the actuator 130, etc.), establishing communication and/or verifying communication between the steering device 110 and the processing system 120, calibrating the steering device 110 with respect to the intravascular device (e.g., establishing a center calibration (e.g., allows the steering device 110 to correct/account for any preset curve of the intravascular device (e.g., due to wear and tear, shipping, reprocessing, etc.) in defining the neutral position of the intravascular device, which can be utilized to provide a straight home position as soon as the steering device is coupled to the intravascular device and powered on; can also be used during manufacturing to reduce scraps and unit to unit variation), compensating for hysteresis of the intravascular device 102, comparing expected actuation responses to actual actuation responses, etc.), activating and/or deactivating one or more program scripts (e.g., a return home function script, a return to stored position function script, a store current position function script, an automated mapping function script, an auto lock function script, a variable speed function script, a multi-level actuation function script, a hysteresis compensation function script, a calibration function script, a remote control function script, and/or combinations thereof); and/or other start-up or set-up procedures.

At block 704, the method 700 includes initiating an operation loop. In the operation loop, the steering device 110 can be utilized to steer an intravascular device 102 coupled to the steering device 110.

At block 706, the method includes determining whether a console override has been activated. In this regard, the system 100 can be configured to control operation of the actuator 130 of the steering device 110 based on inputs to the processing system 120 (e.g., via an associated keyboard, mouse, joystick, touchpad, etc.) or other remote device, which may be described as console operation of the steering device 110. Console operation of the steering device 110 can facilitate remote control of the steering of the intravascular device 102 by a user outside of the procedure room.

If it is determined at block 706 that the console override has been activated (i.e., console operation has been selected), then the method 700 proceeds to block 708 where console operation is performed. In this regard, selection or activation of console operation can cause the handheld operation of the steering device 110 to be disabled or deactivated. However, in some instances both console operation and handheld operation are simultaneously available for steering the intravascular device 102. In console operation, the method 700 includes, at block 710, receiving control inputs from the console and, at block 712, activating the steering actuator 130 based on the control inputs from the console.

The activation of the steering actuator can include running one or more control scripts based on the control inputs from the console. In this regard, the control scripts can be utilized to translate relatively simple control inputs from the console into more complicated steering actuations. For example, the scripts can include such functionality as automatically returning to a home position, automatically returning to a stored position, storing a current position, automatically mapping a vessel, automatically locking a current actuation position, providing variable speed actuation (e.g., speed differentiation through the actuator's range to create smooth and responsive movement throughout the actuation range, eliminating steering dead zones and/or inconsistent responsiveness), providing multi-level actuation (e.g., coarse positioning versus fine positioning), automatically compensating for a detected hysteresis of the intravascular device, and/or combinations thereof. Further, the range of actuation of the steering device 110 can be electronically limited. For example, where inputs to the console are converted into corresponding actuation signals for one or more motor(s) of the actuator 130, the range of the motor(s) can be electronically limited to stay within a desired range of actuation regardless of the control inputs received from the console. In some instances, there is no limitation to the range of actuation.

At block 714, in console operation mode the method includes logging the actuation activity associated with the control inputs from the console. The actuation activity can include a log various parameters associated with the system 100, such as control inputs from the console, status/positions of the actuator of the steering device 110, and/or movement/positions of the intravascular device 102. The log of the actuation activity can be utilized to calibrate the steering device 110 for use with the intravascular device 102. For example, the system can adjust the amount of actuation imparted by the actuator 130 in response to particular control signals from the console to match the actual steering of the intravascular device to the user's expected steering based on the input. This calibration can compensate for steering responsiveness issues associated with the steering device 110, the intravascular device 102, and/or the interface between the steering device 110 and the intravascular device 102. The log of the actuation activity can also be utilized to document procedures, evaluate performance of the steering device 110 and/or intravascular device 102, and/or numerous other analytical analyses. The log of the actuation activity can be utilized within the same procedure and/or a subsequent use of the steering device 110 and/or the intravascular device 102 to improve the control of the steering. In this regard, the method 700 can continue the operation loop by returning to block 706.

If it is determined at block 706 that the console override has not been activated (i.e., handheld operation has been selected), then the method 700 proceeds to block 716 where handheld operation is performed. In this regard, selection or activation of handheld operation can cause the console operation of the steering device 110 to be disabled or deactivated. However, in some instances both handheld operation and console operation are simultaneously available for steering the intravascular device 102. In handheld operation, the method 700 includes, at block 718, receiving control inputs from the handheld controller (e.g., from steering controller 118 of the steering device 110) and, at block 720, activating the steering actuator 130 based on the control inputs from the handheld controller.

The activation of the steering actuator can include running one or more control scripts based on the control inputs from the steering device 110. In this regard, the control scripts can be utilized to translate relatively simple control inputs from the steering device 110 into more complicated steering actuations. For example, the scripts can include such functionality as automatically returning to a home position, automatically returning to a stored position, storing a current position, automatically mapping a vessel, automatically locking a current actuation position, providing variable speed actuation, providing multi-level actuation (e.g., coarse positioning versus fine positioning), automatically compensating for a detected hysteresis of the intravascular device, and/or combinations thereof. Further, the range of actuation of the steering device 110 can be electronically limited. For example, where inputs to the console are converted into corresponding actuation signals for one or more motor(s) of the actuator 130, the range of the motor(s) can be electronically limited to stay within a desired range of actuation regardless of the control inputs received from the console. In some instances, there is no limitation to the range of actuation. It is understood that the same control scripts may be utilized for both console operation and handheld operation in some implementations. In other implementations, separate control scripts are provided for console operation and handheld operation (e.g., to account for the differences between the types of inputs received), but that achieve similar resulting functionality.

At block 722, in handheld operation mode the method includes logging the actuation activity associated with the control inputs from the handheld controller. The actuation activity can include a log various parameters associated with the system 100, such as control inputs from the steering device 110, status/positions of the actuator 130 of the steering device 110, and/or movement/positions of the intravascular device 102. The log of the actuation activity can be utilized to calibrate the steering device 110 for use with the intravascular device 102. For example, the amount of actuation imparted by the actuator 130 in response to particular control signals from the steering controller 118 can be adjusted to match the actual steering of the intravascular device to the user's expected steering based on the input. This calibration can compensate for steering responsiveness issues associated with the steering device 110, the intravascular device 102, and/or the interface between the steering device 110 and the intravascular device 102. The log of the actuation activity can also be utilized to document procedures, evaluate performance of the steering device 110 and/or intravascular device 102, and/or numerous other analytical analyses. The log of the actuation activity can be utilized within the same procedure and/or a subsequent use of the steering device 110 and/or the intravascular device 102 to improve the control of the steering. In this regard, the method 700 can continue the operation loop by returning to block 706. In some instances the log of actuation activity for console operation may be utilized to adjust operating parameters during handheld operation, and vice versa.

Figure 8:
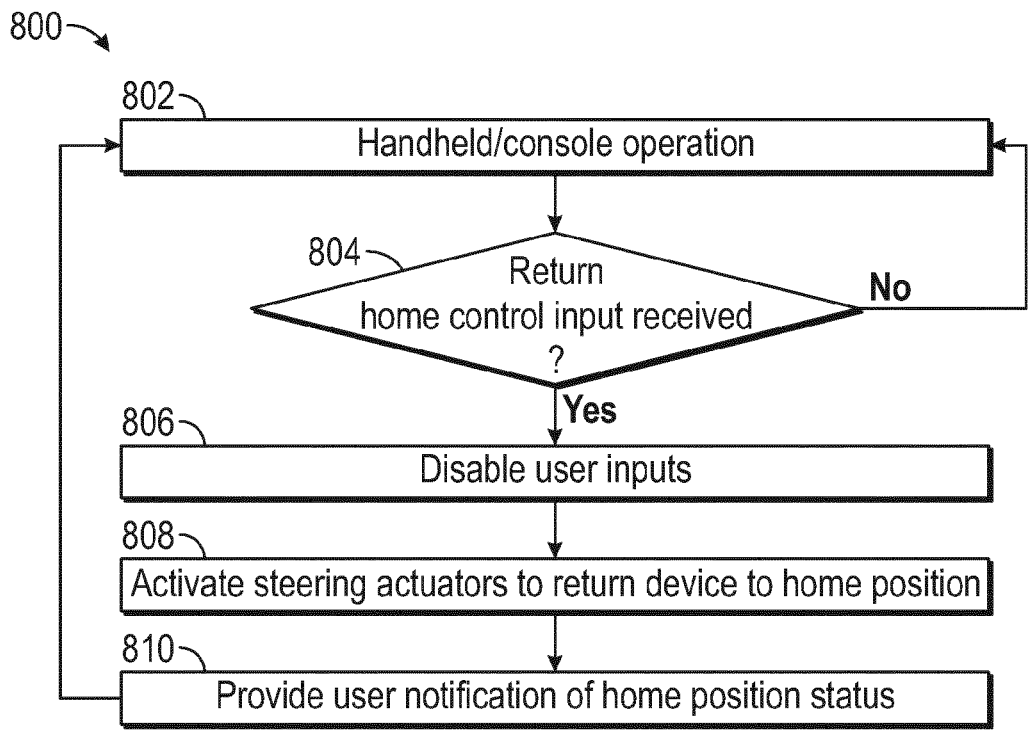
FIG. 8 is a flow chart illustrating aspects of controlling a steering device utilizing a return home control function according to the present disclosure.

Referring now to FIG. 8, shown therein is a flow chart illustrating aspects of a method 800 of controlling a steering device utilizing a return home control function according to the present disclosure. The method 800 may be implemented as part of the console operation (blocks 708-714) and/or the handheld operation (blocks 716-722) of method 700 described above. Accordingly, at block 802, the method 800 includes operating in handheld operation mode and/or console operation mode. At block 804, the method 800 includes determining whether a return home control input has been received. In this regard, the return home control input can include a particular control input and/or a series of control inputs from the handheld controller and/or the console. Generally, any type of input that is detectable and distinguishable from other control inputs may be utilized as the return home control input. In some instances, the handheld device and/or console includes a dedicated input for the return home control input (e.g., a separate button on the handheld device and/or a virtual button on the graphical user interface), such that the steering device 110 automatically returns the intravascular device 102 to the home position upon activation of the dedicated input.

If it is determined at block 804 that a return home control input has not been received, then the method 800 proceeds to block 802 and continues handheld and/or console operation. If it is determined at block 804 that a return home control input has been received, then the method 800 proceeds to block 806, where user control inputs are temporarily disabled. Temporarily disabling the user control inputs allows the steering device 110 to utilize the actuator 130 to return the intravascular device 102 to the home position without interference from new steering control inputs from the user. At block 808, the method 800 includes activating the steering actuators to return the intravascular device to the home position. In this regard, parameters associated with the home position may be saved in memory of the steering device 110 and/or the processing system 120.

At block 810, the method 800 includes providing the user a notification as to the home position status. In some implementations, one or more of the light indicators 144, 146, and 148 may be utilized to provide a status notification to the user. For example, a first light, color (e.g., white), and/or number of blinks can indicate that return home script has been activated, a second light, color (e.g., yellow), and/or number of blinks can indicate that the steering device 110 is in the process of returning to the home position, a third light, color (e.g., green), and/or number of blinks can indicate that the steering device 110 has reached the home position, and/or a fourth light, color (e.g., red), and/or number of blinks can indicate that an error has occurred. Similarly, tactile and/or audible indicators can also be used to convey the home position status to the user. Following block 810, the method 800 continues with handheld and/or console operation at block 802.

Figure 9:
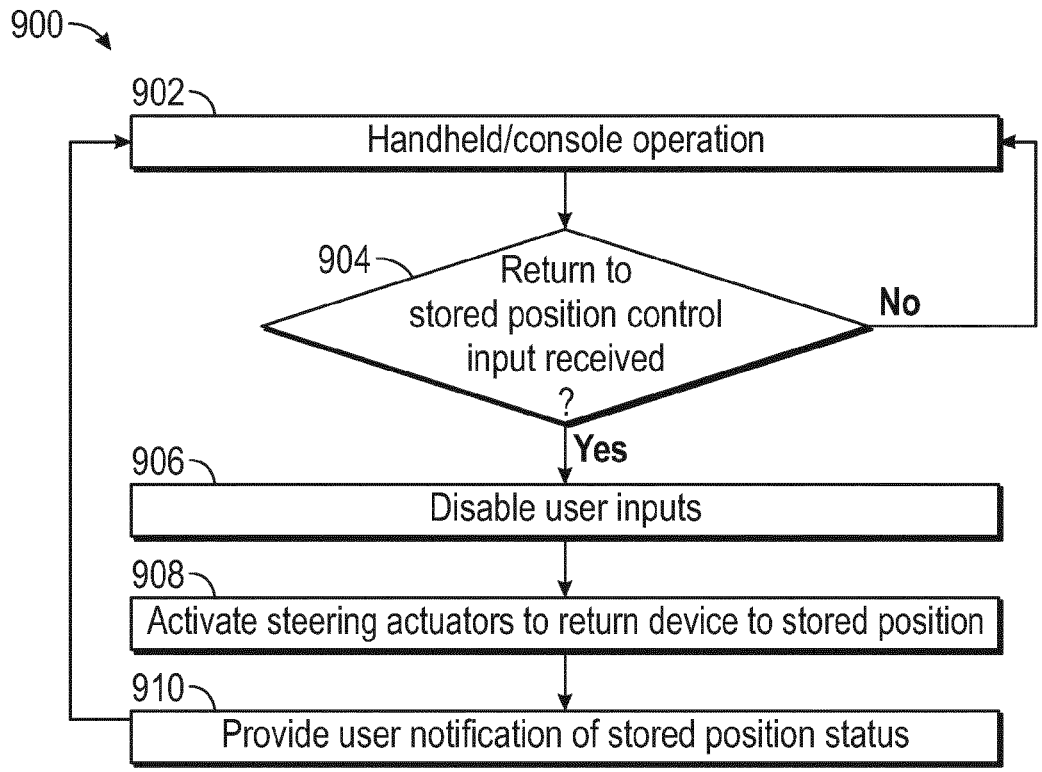
FIG. 9 is a flow chart illustrating aspects of controlling a steering device utilizing a return to a stored position control function according to the present disclosure.

Referring now to FIG. 9, shown therein is a flow chart illustrating aspects of a method 900 of controlling a steering device utilizing a return to a stored position control function according to the present disclosure. The method 900 may be implemented as part of the console operation (blocks 708-714) and/or the handheld operation (blocks 716-722) of method 700 described above. Accordingly, at block 902, the method 900 includes operating in handheld operation mode and/or console operation mode. At block 904, the method 900 includes determining whether a return to stored position control input has been received. In this regard, the return to stored position control input can include a particular control input and/or a series of control inputs from the handheld controller and/or the console. Generally, any type of input that is detectable and distinguishable from other control inputs may be utilized as the return to stored position control input. In some instances, the handheld device and/or console includes a dedicated input for the return to stored position control input (e.g., a separate button on the handheld device and/or a virtual button on the graphical user interface), such that the steering device 110 automatically returns the intravascular device 102 to the stored position upon activation of the dedicated input. In some instances, multiple stored positions may be available and have associated control inputs that cause the steering device 110 to return to a particular one of the stored positions.

If it is determined at block 904 that a return to stored position control input has not been received, then the method 900 proceeds to block 902 and continues handheld and/or console operation. If it is determined at block 904 that a return to stored position control input has been received, then the method 900 proceeds to block 906, where user control inputs are temporarily disabled. Temporarily disabling the user control inputs allows the steering device 110 to utilize the actuator 130 to return the intravascular device 102 to the stored position without interference from new steering control inputs from the user. At block 908, the method 900 includes activating the steering actuators to return the intravascular device to the stored position. In this regard, parameters associated with the stored position may be saved in memory of the steering device 110 and/or the processing system 120.

At block 910, the method 900 includes providing the user a notification as to the stored position status. In some implementations, one or more of the light indicators 144, 146, and 148 may be utilized to provide a status notification to the user. For example, a first light, color (e.g., white), and/or number of blinks can indicate that the return to stored position script has been activated, a second light, color (e.g., yellow), and/or number of blinks can indicate that the steering device 110 is in the process of returning to the stored position, a third light, color (e.g., green), and/or number of blinks can indicate that the steering device 110 has reached the stored position, and/or a fourth light, color (e.g., red), and/or number of blinks can indicate that an error has occurred. Similarly, tactile and/or audible indicators can also be used to convey the stored position status to the user. Following block 910, the method 900 continues with handheld and/or console operation at block 902.

Figure 10:
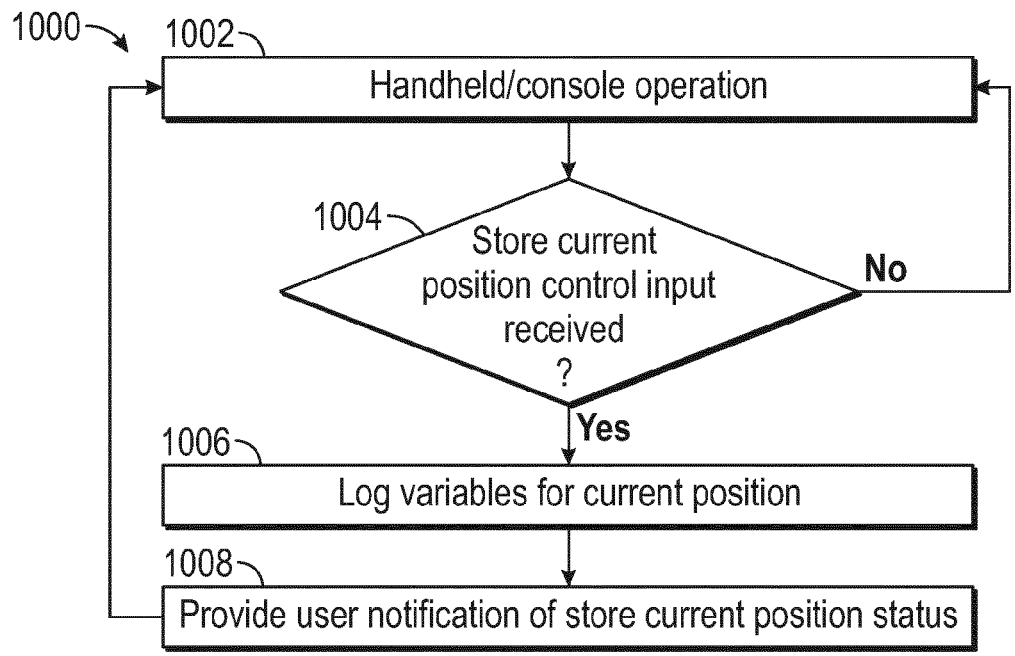
FIG. 10 is a flow chart illustrating aspects of controlling a steering device utilizing a store current position function according to the present disclosure.

Referring now to FIG. 10, shown therein is a flow chart illustrating aspects of a method 1000 of controlling a steering device utilizing a store current position function according to the present disclosure. The method 1000 may be implemented as part of the console operation (blocks 708-714) and/or the handheld operation (blocks 716-722) of method 700 described above. Accordingly, at block 1002, the method 1000 includes operating in handheld operation mode and/or console operation mode. At block 1004, the method 900 includes determining whether a store current position control input has been received. In this regard, the store current position control input can include a particular control input and/or a series of control inputs from the handheld controller and/or the console. Generally, any type of input that is detectable and distinguishable from other control inputs may be utilized as the store current position control input. In some instances, the handheld device and/or console includes a dedicated input for the store current position control input (e.g., a separate button on the handheld device and/or a virtual button on the graphical user interface).

If it is determined at block 1004 that a store current position control input has not been received, then the method 1000 proceeds to block 1002 and continues handheld and/or console operation. If it is determined at block 1004 that a store current position control input has been received, then the method 1000 proceeds to block 1006, where variables associated with the current position are logged. In this regard, the variables/parameters associated with the stored position may be saved in memory of the steering device 110 and/or the processing system 120. In some instances, variables/parameters associated with multiple stored positions are saved in memory. In such instances, the user may select and/or the system may automatically determine whether the variables/parameters of the current position should overwrite the variables/parameters associated with a previously stored position and/or be stored separately as a new position. Generally, any objectively measurable or detectable variables/parameters of the system associated with the current position may be stored. The variables/parameters may include one or more of: actuator status (e.g., on/off, position, tension, force, pressure, etc.), steering controller status (e.g., current position, recent positions, current control input(s), recent control input(s), etc.), intravascular device status (e.g., position, orientation, tension, force, pressure, etc.), and/or combinations thereof.

At block 1008, the method 1000 includes providing the user a notification as to the store current position status. In some implementations, one or more of the light indicators 144, 146, and 148 may be utilized to provide a status notification to the user. For example, a first light, color (e.g., white), and/or number of blinks can indicate that the store current position script has been activated, a second light, color (e.g., yellow), and/or number of blinks can indicate that the steering device 110 is in the process of storing the variables/parameters associated with the current position, a third light, color (e.g., green), and/or number of blinks can indicate that the steering device 110 has stored the variables/parameters associated with the current position, and/or a fourth light, color (e.g., red), and/or number of blinks can indicate that an error has occurred. Similarly, tactile and/or audible indicators can also be used to convey the store current position status to the user. Following block 1008, the method 1000 continues with handheld and/or console operation at block 1002.

Figure 11:
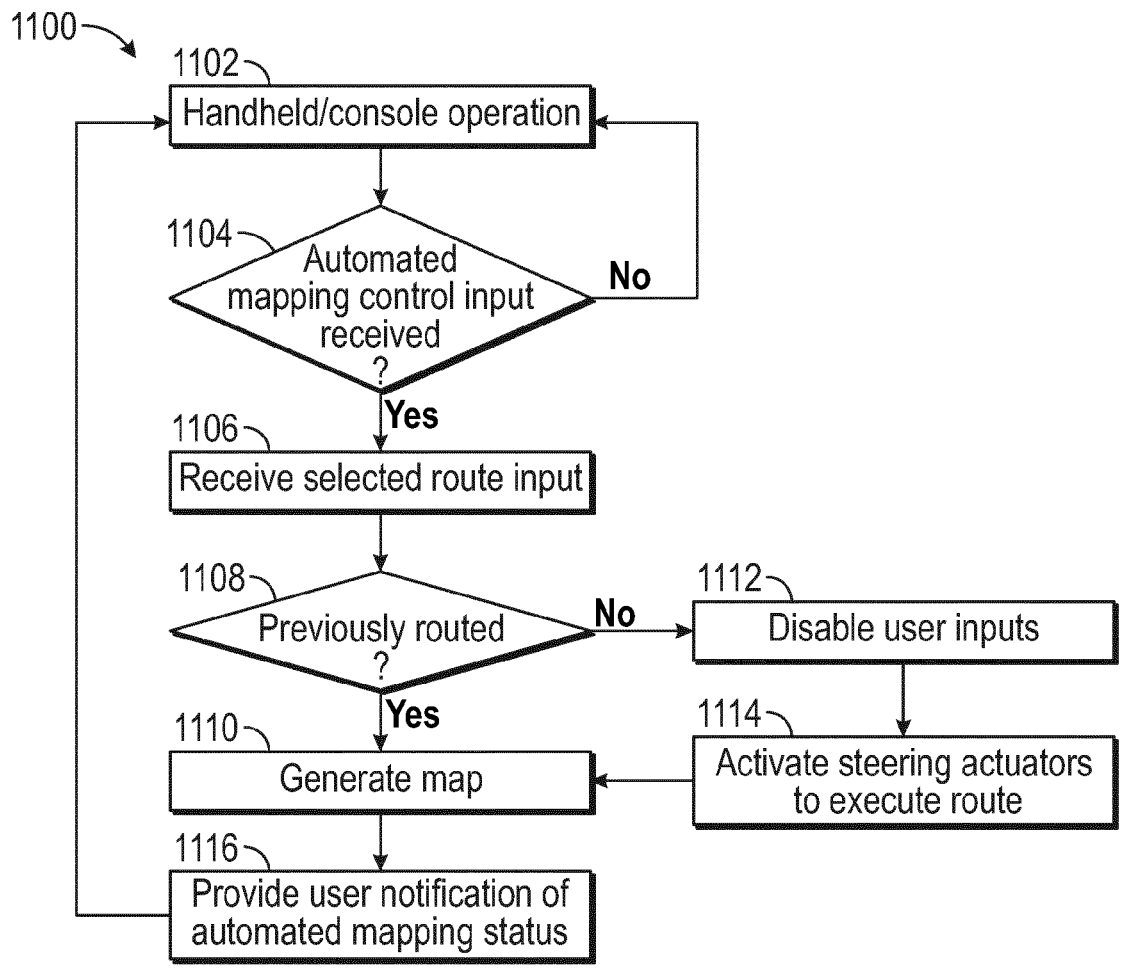
FIG. 11 is a flow chart illustrating aspects of controlling a steering device utilizing an automated mapping function according to the present disclosure.

Referring now to FIG. 11, shown therein is a flow chart illustrating aspects of a method 1100 of controlling a steering device utilizing an automated mapping function according to the present disclosure. The method 1200 may be implemented as part of the console operation (blocks 708-714) and/or the handheld operation (blocks 716-722) of method 700 described above. Accordingly, at block 1102, the method 1100 includes operating in handheld operation mode and/or console operation mode. At block 1104, the method 1100 includes determining whether an automated mapping control input has been received. In this regard, the automated mapping control input can include a particular control input and/or a series of control inputs from the handheld controller and/or the console. Generally, any type of input that is detectable and distinguishable from other control inputs may be utilized as the automated mapping control input. In some instances, the handheld device and/or console includes a dedicated input for the automated mapping control input (e.g., a separate button on the handheld device and/or a virtual button on the graphical user interface).

If it is determined at block 1104 that an automated mapping control input has not been received, then the method 1100 proceeds to block 1102 and continues handheld and/or console operation. If it is determined at block 1104 that an automated mapping control input has been received, then the method 1100 proceeds to block 1106, where a selected route input is received. In this regard, the selected route may identify a region of interest within the patient's vessel for which automated mapping is desired. In this regard, the route may include regions of the vessel through which the intravascular device has already been steered or previously routed and obtained data for as well as regions of the vessel through which the intravascular device has not been steered or previously routed (or during which the sensing element of the intravascular device was not activated).

At block 1108, it is determined whether the selected route was previously routed while the intravascular device 102 obtained data. If it is determined at block 1108 that the intravascular device has previously traveled the selected route and obtained corresponding data, then the method 1100 proceeds to block 1110.

At block 1110, the method 1100 includes generating a map. In this regard, the automated mapping can synchronize or co-register the data collected by the intravascular device with the corresponding actuator positions when the intravascular device was positioned within and/or moving along the region of interest. In this regard, the data from the intravascular device can include thermal sensing data that can be used to generate a thermal map, IVUS, OCT, ICE, and/or photo-acoustic imaging data that can be used to generate a 3D anatomical map, pressure sensing data that can be used to generate a pressure map, etc. If additional precision is desired with regards to the correlation between actuator position and the intravascular device position/state, a gyrometer/accelerometer can be integrated into the actuator of the steering device 110 and utilized to correlate the data obtained by the intravascular device with the position of the intravascular device at the time the data was obtained.

If it is determined at block 1108 that the intravascular device has not previously traveled the selected route and obtained corresponding data, then the method 1100 proceeds to block 1112. At block 1112, user control inputs are temporarily disabled. Temporarily disabling the user control inputs allows the steering device 110 to utilize the actuator 130 move the intravascular device 102 along the selected route without interference from new steering control inputs from the user. At block 1114, the method 1100 includes activating the steering actuators to execute the selected route. Following block 1114, the method 1100 continues to block 1110 where a map is generated.

At block 1116, the method 1100 includes providing the user a notification as to the automated mapping status. In some implementations, one or more of the light indicators 144, 146, and 148 may be utilized to provide a status notification to the user. For example, a first light, color (e.g., white), and/or number of blinks can indicate that the automated mapping script has been activated, a second light, color (e.g., yellow), and/or number of blinks can indicate that the automated mapping is in process, a third light, color (e.g., green), and/or number of blinks can indicate that automated mapping has been completed, and/or a fourth light, color (e.g., red), and/or number of blinks can indicate that an error has occurred. Similarly, tactile and/or audible indicators can also be used to convey the automated mapping status to the user. Following block 1116, the method 1100 continues with handheld and/or console operation at block 1102.

Figure 12:
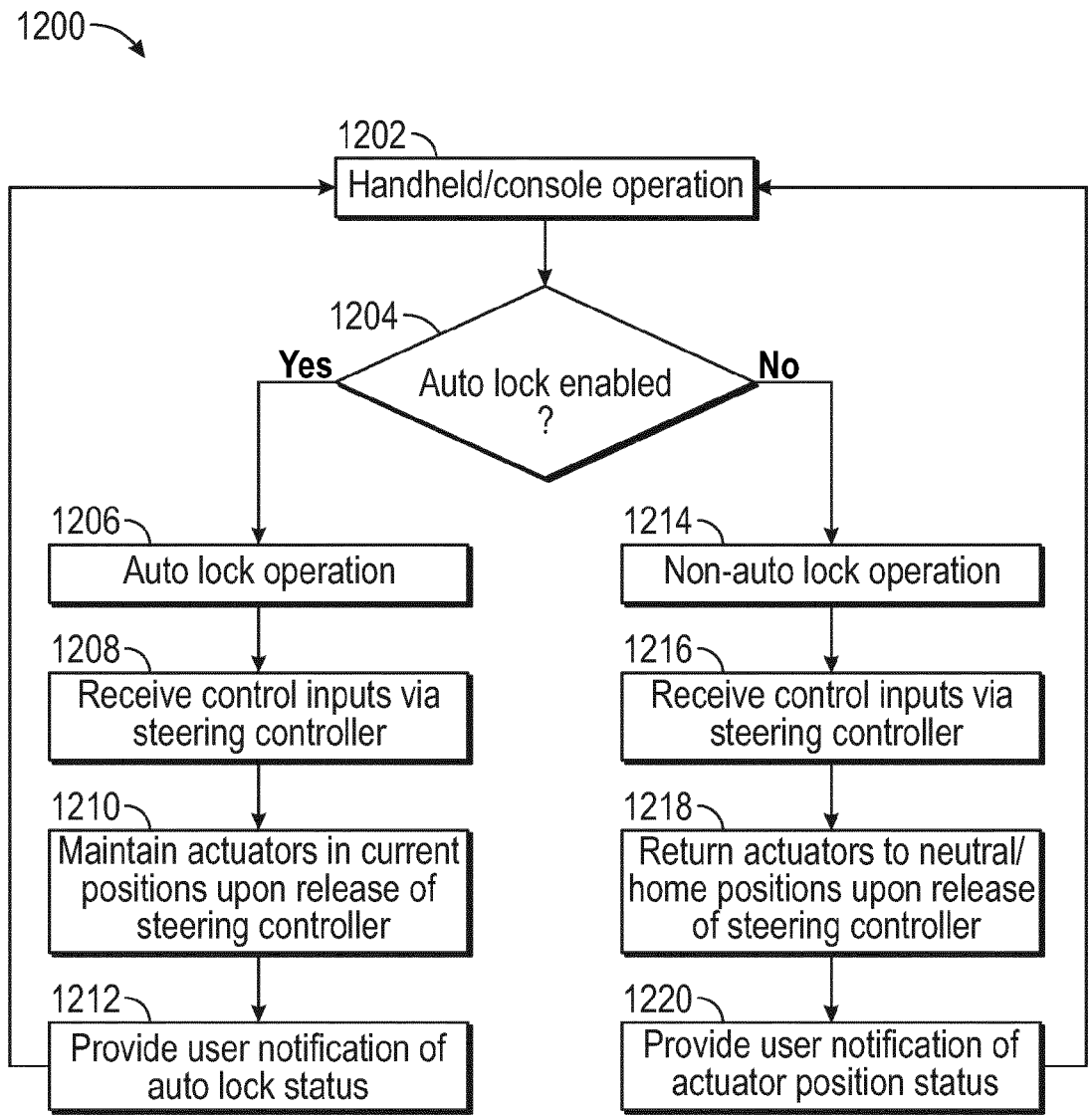
FIG. 12 is a flow chart illustrating aspects of controlling a steering device utilizing an auto lock function according to the present disclosure.

Referring now to FIG. 12, shown therein is a flow chart illustrating aspects of a method 1200 of controlling a steering device utilizing an auto lock function according to the present disclosure. The method 1200 may be implemented as part of the console operation (blocks 708-714) and/or the handheld operation (blocks 716-722) of method 700 described above. Accordingly, at block 1202, the method 1200 includes operating in handheld operation mode and/or console operation mode. At block 1204, the method 1200 includes determining whether an auto lock function has been enabled. In this regard, the auto lock function can be automatically and/or selectively activated based on user input, steering device properties, and/or intravascular device properties.

If it is determined at block 1204 that the auto lock function has been activated/enabled, then the method 1200 proceeds to block 1206, where auto lock operation is initiated. At block 1208, control inputs are received from a steering controller (e.g., steering device 110 and/or the processing system 120). At block 1210, the method 1200 includes maintaining the actuator 130 in the current position upon release of the steering controller and/or receipt of the control inputs from the steering controller. In this regard, the auto lock function causes the steering device 110 to hold or maintain the actuated state of the actuator 130 upon release of the steering controller (e.g., the joystick) and/or return of the steering controller back to its neutral position.

At block 1212, the method 1200 includes providing the user a notification as to the auto lock status. In some implementations, one or more of the light indicators 144, 146, and 148 may be utilized to provide a status notification to the user. For example, a first light, color (e.g., white), and/or number of blinks can indicate that the auto lock script has been activated, a second light, color (e.g., yellow), and/or number of blinks can indicate that the steering controller is in use and that the auto lock function will be implemented upon release of the steering controller, a third light, color (e.g., green), and/or number of blinks can indicate that the auto lock function has been completed, and/or a fourth light, color (e.g., red), and/or number of blinks can indicate that an error has occurred. Similarly, tactile and/or audible indicators can also be used to convey the auto lock status to the user. Following block 1212, the method 1200 continues with handheld and/or console operation at block 1202.

If it is determined at block 1204 that the auto lock function has not been activated/enabled, then the method 1200 proceeds to block 1214, where non-auto lock operation is initiated. At block 1216, control inputs are received from a steering controller (e.g., steering device 110 and/or the processing system 120). At block 1218, the method 1200 includes returning the actuator 130 to a neutral/home position upon release of the steering controller and/or receipt of the control inputs from the steering controller. In this regard, since the auto lock function is not enabled, the steering device 110 does not hold or maintain the actuated state of the actuator 130 upon release of the steering controller (e.g., the joystick) and/or return of the steering controller back to its neutral position. Instead, the steering device 110 allows the actuator 130 to return to a neutral/home position. In some implementations, the steering device 110 limits the rate at which the actuator 130 returns to a neutral/home position to prevent unwanted whipping and/or snapping of the intravascular device 102 or the actuator 130.

At block 1220, the method 1200 includes providing the user a notification as to the actuator position status. In some implementations, one or more of the light indicators 144, 146, and 148 may be utilized to provide a status notification to the user. For example, a first light, color (e.g., green), and/or number of blinks can indicate that the actuator is within an acceptable range of safe positions, a second light, color (e.g., yellow), and/or number of blinks can indicate that the actuator is within, but near the border of the acceptable range of safe positions, and/or a third light, color (e.g., red), and/or number of blinks can indicate that the actuator is outside of the acceptable range of safe positions or that an error has occurred. Similarly, tactile and/or audible indicators can also be used to convey the actuator position status to the user. Following block 1220, the method 1200 continues with handheld and/or console operation at block 1202.

Figure 13:
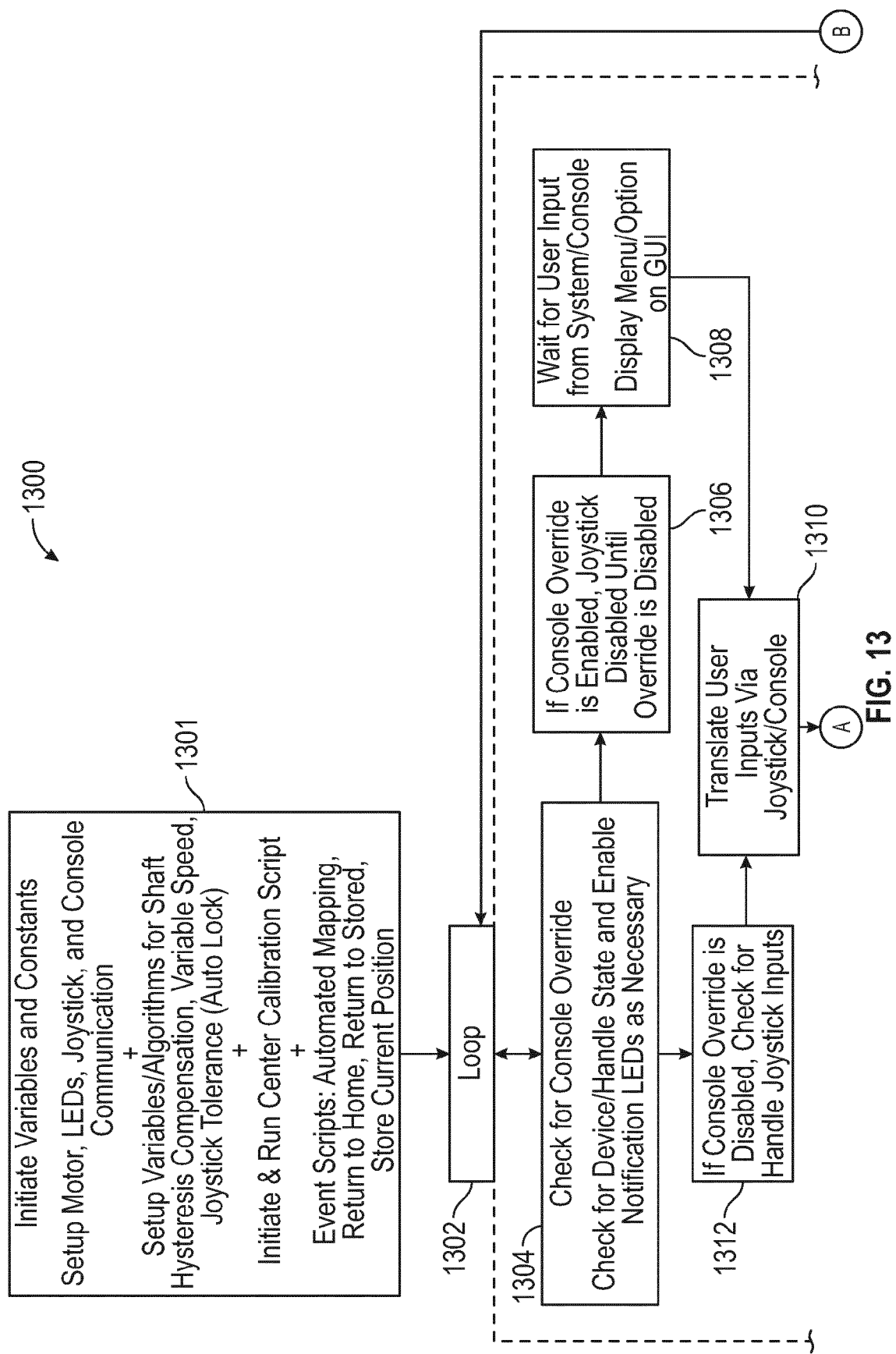
FIG. 13 is a flow chart illustrating an exemplary code architecture for controlling a steering device according to the present disclosure.
Figure 13:
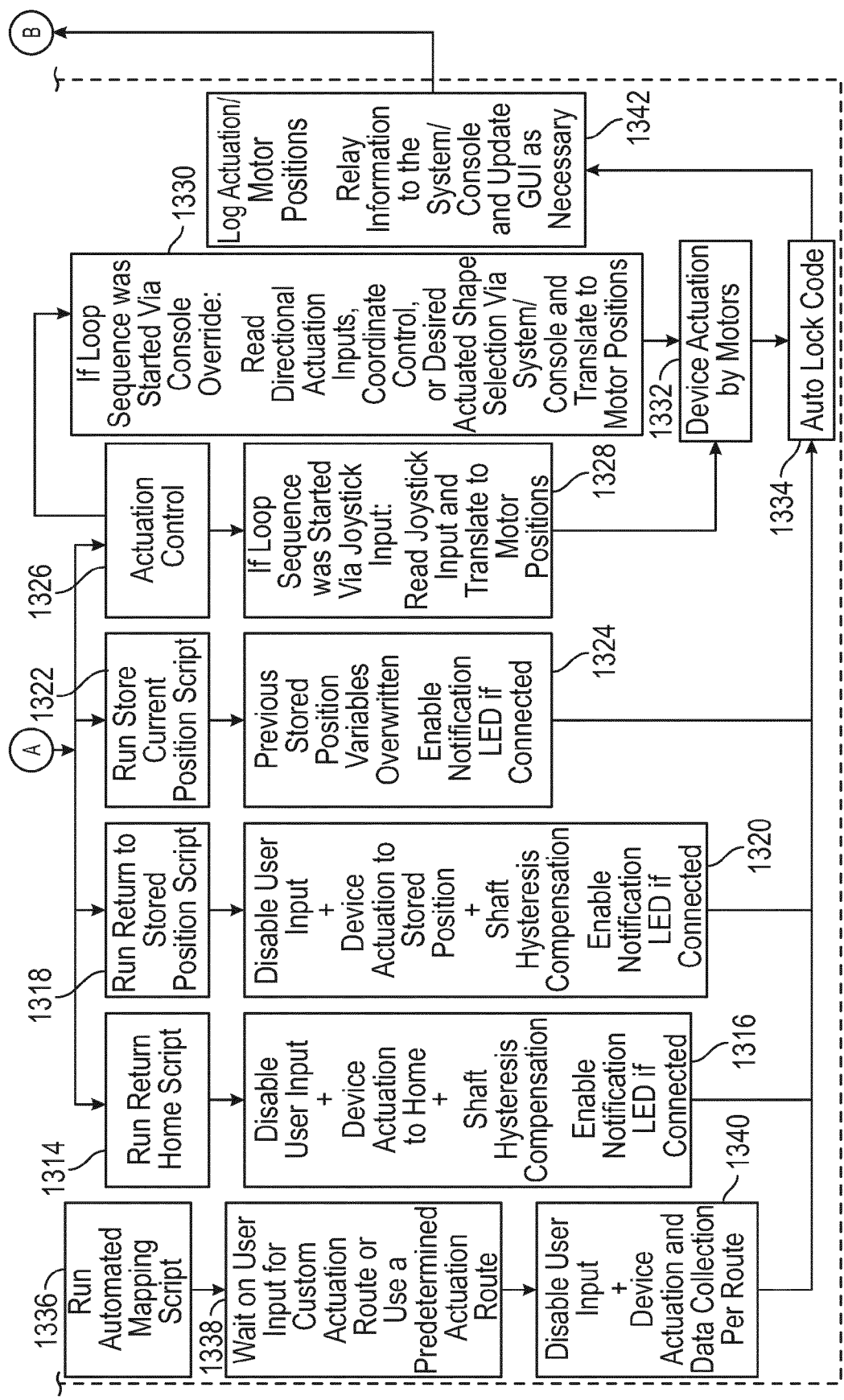

Referring now to FIG. 13, shown therein is a flow chart illustrating an exemplary code architecture 1300 for controlling a steering device according to the present disclosure. In this regard, the code architecture 1300 may be utilized to implement one or more of the methods 700, 800, 900, 1000, 1100, and 1200 described above. In this regard, the code architecture 1300 includes a start-up sequence 1301 and an operation loop 1302.

The start-up sequence 1301 can include: providing power to the steering device 110, including activating the steering controller 118, actuator 130, microcontroller 140, and/or indicator lights 144, 146, and 148; establishing communication and/or verifying communication between the components of the steering device 110 (e.g., between the steering controller 118 and microcontroller 140, between the microcontroller 140 and the actuator 130, etc.), establishing communication and/or verifying communication between the steering device 110 and the processing system 120, calibrating the steering device 110 with respect to the intravascular device (e.g., establishing a center calibration, compensating for hysteresis of the intravascular device 102, comparing expected actuation responses to actual actuation responses, etc.), activating and/or deactivating one or more program scripts (e.g., a return home function script, a return to stored position function script, a store current position function script, an automated mapping function script, an auto lock function script, a variable speed function script, a multi-level actuation function script, a hysteresis compensation function script, a calibration function script, a remote control function script, and/or combinations thereof); and/or other start-up or set-up procedures.

The operation loop 1302 can include numerous control scripts to facilitate handheld operation and/or console operation of the steering device 110. The particular control scripts and arrangements illustrated are for exemplary purposes and do not limit the particular manner in which the control features can be implemented in accordance with the present disclosure. The operation loop 1302 includes code 1304 for determining whether a console override has been enabled, including checking the state of the intravascular device 102, steering device 110, and/or processing system 120 and activating the light indicators 144, 146, and 148 as needed. The operation loop 1302 includes code 1306 for disabling the steering controller 118 of the steering device 110 if the console override has been enabled and keeping the steering controller disabled until console override is disabled. The operation loop 1302 includes code 1308 for waiting and receiving for user inputs from the console/processing system 120 and displaying associated menus and options on a graphical user interface of the console/processing system 120 when the console override has been enabled. The operation loop 1302 includes code 1310 for translating control inputs received via the console/processing system 120 into actuation signals for the actuator 130 of the steering device. The operation loop 1302 includes code 1312 for waiting for and receiving user inputs from the steering controller 118 of the steering device. The operation loop 1302 includes code 1310 for translating control inputs received via the steering device 110 into actuation signals for the actuator 130 of the steering device.

The code 1310 for translating control inputs received via the steering device 110 and/or the console/processing system 120 into actuation signals for the actuator 130 of the steering device can be configured to execute one or more control scripts associated with particular features of the system. For example, in the illustrated embodiment a return home script 1314 can be provided that includes code 1316 to cause the steering device 110 to execute a return home function, including temporarily disabling user inputs, causing the actuator 130 to return to a home position, compensating for intravascular device hysteresis, and/or enabling associated user notifications. A return to stored position script 1318 can be provided that includes code 1320 to cause the steering device 110 to execute a return to stored position function, including temporarily disabling user inputs, causing the actuator 130 to return to a previously stored position, compensating for intravascular device hysteresis, and/or enabling associated user notifications. A store current position script 1322 can be provided that includes code 1324 to cause the steering device 110 to store variables/parameters associated with the current position, including over-writing previously stored position variables/parameters and/or enabling associated user notifications.

The operation loop 1302 includes code 1326 for controlling the actuator 130 of the steering device 110. In this regard, code 1326 can execute code 1328 when the steering device 110 is being utilized to steer and can execute code 1330 when the console/processing system 120 is being utilized to steer. In this regard, the code 1328 can translate the control inputs from the steering device 110 into actuation signals for the actuator 130 of the steering device. Similarly, code 1330 can translate the control inputs from the console/processing system 120 into actuation signals for the actuator 130 of the steering device. Code 1332 can cause the actuator 130 to execute the actuation signals generated by code 1328 and/or code 1330 to steer the intravascular device 102. The operation loop can also include code 1334 for executing (or not) an auto lock function depending on whether the auto lock function has been enabled (or disabled).

The operation loop 1302 also includes an automated mapping script 1336 that includes code 1336 for waiting on a user input for a custom actuation route and/or a predetermined actuation route associated with the mapping. The automated mapping script 1336 can also include code 1340 to cause the steering device 110 to execute a selected mapping route, including temporarily disabling user inputs, causing the actuator 130 to execute the selected route, cause the intravascular device to collect data during the route, compensate for intravascular device hysteresis, and/or enabling associated user notifications regarding the automated mapping.

The operation loop 1302 also includes code 1342 for logging actuation parameters during use of the steering device 110. The code 1342 can also communicate some or all of the logged parameters to the console/processing system 120. The code 1342 can also cause the console/processing system 120 to update one or more aspects of a graphical user interface to reflect the logged actuation parameters. The code and scripts of the operation loop 1302 can be repeated, as needed, to facilitate operation of the steering device 110 and its associated control features.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular steering device, comprising:
   a housing including a proximal portion and a distal portion, wherein the distal portion includes an opening sized and shaped to receive an intravascular device;
   a steering controller coupled to the housing and configured to receive a first user input for a manual control of the intravascular device;
   a processor in communication with the steering controller, the processor configured to generate, based on a code architecture stored in a memory for execution by the processor, a first actuation signal and a second actuation signal,
      wherein the first actuation signal is generated by translating the first user input from the steering controller based on the code architecture,
      wherein the second actuation signal corresponds to an automated control comprising a sequence of predetermined actions to be performed by the intravascular device, wherein the code architecture includes a script describing the sequence of predetermined actions, wherein the sequence of predetermined actions to be performed comprises at least one of a return home function, a return to stored position function, or an automated mapping function,
      wherein the script, when executed by the processor, directs the processor to electronically disable the first user input from the steering controller during a time period between receipt of a second user input to execute the automated control and completion of the automated control such that, during the time period, the processor is configured to provide only the second actuation signal; and
   an actuator positioned within the housing and in communication with the processor such that the actuator receives the first actuation signal and the second actuation signal from the processor, the actuator configured to interface with the intravascular device based on the first actuation signal and the second actuation signal to steer the intravascular device, wherein the housing is sized and shaped for grasping by a hand of a user while the sequence of predetermined actions is performed.

2. The intravascular steering device of claim 1, wherein the actuator includes:
   a first mechanism for controlling movement in a first dimension;
   a second mechanism for controlling movement in a second dimension perpendicular to the first dimension; and
   a third mechanism for controlling rotation of the intravascular device about a longitudinal axis of the intravascular device, the longitudinal axis being perpendicular to the first and second dimension.

3. The intravascular steering device of claim 1, wherein the processor is positioned within the housing.

4. The intravascular steering device of claim 1, wherein the processor is positioned remote from the housing.

5. The intravascular steering device of claim 1, further comprising:
   a haptic feedback device positioned within the housing, the haptic feedback device configured to provide an alert to a user when a force on the intravascular device exceeds a threshold.

6. The intravascular steering device of claim 5, wherein the force on the intravascular device is measured by a sensor located within at least one of the housing and the intravascular device.

7. The intravascular steering device of claim 1, further comprising:
   a rechargeable power supply positioned within the housing; and
   a wireless transceiver positioned within the housing.

8. An intravascular steering device, comprising:
   a housing including a proximal portion and a distal portion, wherein the distal portion includes an opening sized and shaped to receive an intravascular device;
   a steering controller coupled to the housing and configured to receive a first user input;
   processor in communication with the steering controller, the processor configured to generate an actuation signal based on a code architecture stored in a memory for execution by the processor, wherein the actuation signal corresponds to an automated control comprising a sequence of predetermined actions to be performed by the intravascular device, wherein the code architecture comprises a script describing the sequence of predetermined actions, wherein the sequence of predetermined actions to be performed comprises at least one of a return home function, a return to stored position function, or an automated mapping function,
   wherein the script, when executed by the processor, directs the processor to electronically disable the first user input from the steering controller during a time period between receipt of a second user input to execute the automated control and completion of the automated control such that, during the time period, the processor is configured to provide only the actuation signal; and
   an actuator positioned within the housing and in communication with the processor such that the actuator receives the actuation signal from the processor, the actuator configured to interface with the intravascular device based on the actuation signal to steer the intravascular device,
   wherein the housing is sized and shaped for grasping by a hand of a user while the sequence of predetermined actions is performed.

9. The intravascular steering device of claim 8, wherein the sequence of predetermined actions performs the return home function that returns the intravascular device to a home position.

10. The intravascular steering device of claim 8, wherein the sequence of predetermined actions performs the return to stored position function that returns the intravascular device to a previously-stored position.

11. The intravascular steering device of claim 8, wherein the code architecture further directs the processor to store a position of the intravascular device.

12. The intravascular steering device of claim 11, wherein the sequence of predetermined actions performs the return to stored position function that guides the intravascular device to the stored position of the intravascular device.

13. The intravascular steering device of claim 8, wherein the sequence of predetermined actions performs the automated mapping function that guides the intravascular device along a previously-mapped route.

14. The intravascular steering device of claim 8, wherein the actuator includes:
   a first mechanism for controlling movement in a first dimension;
   a second mechanism for controlling movement in a second dimension perpendicular to the first dimension; and
   a third mechanism for controlling rotation of the intravascular device about a longitudinal axis of the intravascular device, the longitudinal axis being perpendicular to the first and second dimension.

15. The intravascular steering device of claim 8,
   wherein the sequence of predetermined actions performs the automated mapping function that guides the intravascular device along a region of interest of a vessel,
   wherein the automated mapping function synchronizes data collected by the intravascular device with corresponding actuator positions when the intravascular device was positioned within the region of interest, and
   wherein the synchronized data is used to generate a three-dimensional anatomical map.

* * * * *